(12) United States Patent
Otvos

(10) Patent No.: US 6,653,140 B2
(45) Date of Patent: Nov. 25, 2003

(54) METHODS FOR PROVIDING PERSONALIZED LIPOPROTEIN-BASED RISK ASSESSMENTS

(75) Inventor: James D. Otvos, Apex, NC (US)

(73) Assignee: Liposcience, Inc., Raleigh, NC (US)

( * ) Notice: Subject to any disclaimer, the term of this patent is extended or adjusted under 35 U.S.C. 154(b) by 0 days.

(21) Appl. No.: 10/294,262

(22) Filed: Nov. 14, 2002

(65) Prior Publication Data

US 2003/0119194 A1 Jun. 26, 2003

Related U.S. Application Data

(63) Continuation of application No. 09/258,740, filed on Feb. 26, 1999, now abandoned.

(51) Int. Cl.[7] ............................................. G01N 33/92
(52) U.S. Cl. ........................ 436/71; 436/13; 436/16; 436/173
(58) Field of Search ............................. 436/13, 16, 71, 436/173

(56) References Cited

U.S. PATENT DOCUMENTS

| | | | |
|---|---|---|---|
| 4,933,844 A | 6/1990 | Otvos | 364/413.08 |
| 5,343,389 A | 8/1994 | Otvos | 364/413.09 |

FOREIGN PATENT DOCUMENTS

| | | |
|---|---|---|
| WO | WO 91/10128 | 7/1991 |
| WO | WO 93/03450 | 2/1993 |

OTHER PUBLICATIONS

News Release, *Radio signals give new spectrum for cholesterol lipoprotein readings*, American Heart Association Journal Report (Jul. 9, 1998).
Brochure, *New Technology Detects Hidden Risk of Heart Disease; NMR Lipoprofile™ Seen as Powerful New Tool in Disease Assessment and Management*, LipoMed, Inc., Raleigh, NC (Mar. 26, 1998).
Abstracts, Supplement to Circulation, Journal of the Americn Heart Association Abstracts for the 71st Scientific Sessions (11/98).
Otvos, *Measurement of Lipoprotein Subclass Profiles by NMR Spectroscopy*, Handbook of Lipoprotein Testing, pp. 497–508 (AACC Press, 1997).
Freedman et al., *Relation of Lipoprotein Subclasses as Measured by Proton Nuclear Magnetic Resonance Spectroscopy to Coronary Artery Disease*, Arterioscler Thromb Vasc Biol. 18, pp. 1046–1053 (Jul. 1998).
Wilson et al., *Prediction of Coronary Heart Disease Using Risk Factor Categories*, American Heart Association, Inc. pp. 1837–1847 (5/98).
National Cholesterol Education Program, "Second Report of the Expert Panel on Detection, Evaluation, and Treatment of High Blood Cholesterol in Adults (Adult Treatment Panel II)," Circulation 1994, vol. 89, No. 3 (pp. 1329–1445 (Mar. 1994).
Lamarche et al., "Apolipoprotein A–I and B Levels and the Risk of Ischemic Heart Disease During a Five–Year Follow–up of Men in the Québec Cardiovascular Study," Circulation, vol. 94, No. 3, pp. 273–278 (Aug. 1, 1996).

(List continued on next page.)

*Primary Examiner*—Jill Warden
*Assistant Examiner*—Yelena Gakh
(74) *Attorney, Agent, or Firm*—Myers Bigel Sibley & Sajovec PA

(57) ABSTRACT

Methods for assessing a patient's risk of having or developing coronary heart disease based on lipoprotein measurements measure and identify values for lipoprotein subclass constituents and analyze according to predetermined test criteria to identify when there is an increased and/or decreased risk of having and/or developing coronary heart disease associated wit the measured lipoprotein subclass constituent values.

23 Claims, 11 Drawing Sheets

OTHER PUBLICATIONS

Wilson, et al., "Impact of National Guidelines for Cholesterol Risk Factor Screening," JAMA, vol. 262, No. 1, pp. 41–44 (Jul. 7, 1989).

"Magnetic Resonance Test May Give Better Assessment of Heart Disease Risk," Doctor's Guide, Online, pp. 1–3, url:httpp://www.pslgroup.com/dg8DE5A.htm (Jun. 8, 2000).

"Company Profile: LipoMed Technology Anticipated to be a Leading Predictor of Heart Disease," BT Catalyst, Online, pp. 1–3, url:htt;//www.ncbiotech.org/feb98–4.hum (Jun. 8, 2000).

"New Test More Accurately Measures Risk of Heart Disease, Study Finds,"NC State University Document View, Online, pp. 1–6 (Jul. 13, 1998, url:http://search.ncsu.edu (Jun. 8, 2000).

Ala–Korpela et al., "Quantification of Biomedical NMR Data Using Artificial Neural Network Analysis: Lipoprotein Lipid Profiles from $^1$H NMR Data of Human Plasma," NMR in Biomedicine, GB, Wiley, London, vol. 8, No. 6, pp. 235–244 (Sep. 1, 1995).

PCT International Search Report, International Application No. PCT/US99/29730, mailed Jul. 6, 2000.

Summary Report

| Patient Name | Patient ID |
|---|---|
| Jane Doe | RP21-3947 |

| Specimen ID | Date Collected | Date Received | Date Reported |
|---|---|---|---|
| LM99-1402 | 01-25-99 | 01-26-99 | 01-27-99 |

| Sex | Age | Blood Pressure | Diabetes | Smoker |
|---|---|---|---|---|
| F | 53 | 132/86 | No | Yes |

Physician Name & Address

Phone: ( )
FAX: ( )

Comments

LIPID PROFILE*

Current NCEP Guidelines for Primary Prevention

| | mg/dL | Desirable | Borderline-High | High |
|---|---|---|---|---|
| Total Cholesterol | 230 | less than 200 | 200-239 | 240 or greater |
| LDL Cholesterol | 165 | less than 130 | 130-159 | 160 or greater |

| | | Negative Risk Factor | Intermediate | Positive Risk Factor |
|---|---|---|---|---|
| HDL Cholesterol | 42 | 60 or greater | 35-59 | less than 35 |

| | | Desirable | Borderline-High | High |
|---|---|---|---|---|
| Triglycerides | 160 | less than 200 | 200-400 | 400-1,000 |

* Lipid profile values are derived from direct NMR measurement of plasma lipoproteins, not from standard lipid tests. For most patients, NMR and standard lipid panel values agree closely. Some patients with metabolic abnormalities or elevated triglycerides have abnormally cholesterol-poor LDL particles. Their LDL cholesterol levels when measured by standard tests will be lower than determined by NMR. The NMR values more closely reflect the actual number of LDL particles in the circulation.

SUBCLASS PROFILE

| | nm | Pattern A (large) | Pattern AB (Intermediate) | Pattern B (small) |
|---|---|---|---|---|
| LDL Size | 19.6 | 20.6-22.0 | 20.4-20.5 | 19.0-20.3 |
| | | Lower-Risk | | Higher-Risk |

| | nmol/L | Percentage of population with a lower level | |
|---|---|---|---|
| LDL Particles | 2205 | Lower ← CHD Risk → Higher | (94%) |

| | mg/dL | Percentage of population with a higher level | |
|---|---|---|---|
| Large HDL Cholesterol | 21 | Lower ← CHD Risk → Higher | (71%) |

| | mg/dL | Percentage of population with a lower level | |
|---|---|---|---|
| Large VLDL Trygyceride | 30 | Lower ← CHD Risk → Higher | (78%) |

Population percentages are based on data obtained from analysis of 3,437 subjects in the Framingham Offspring Study.

© LipoScience, Inc. 02/99

FIG. 1

Risk Assessment Report

| Patient Name | Specimen ID | Date Reported |
|---|---|---|
| Jane Doe | LM99-1402 | 01-27-99 |

Supplemental Risk Factors
CHD risk can increase significantly when there is a clustering of metabolic abnormalities not detected by standard lipid tests. A check mark in multiple boxes below suggests the patient has a metabolic profile associated with a higher level of risk.

| | | |
|---|---|---|
| Small LDL | Pattern B ✓ | Small LDL (Pattern B) is a hallmark of the "atherogenic lipoprotein phenotype" and confers about 3 to 4-fold higher risk compared to the large LDL trait (Pattern A). Evidence suggests that small LDL particles may be inherently more atherogenic than large LDL. |
| Elevated Number of LDL Particles | Upper 33% ✓ | Unlike LDL cholesterol, LDL particle concentration (related closely to plasma apo B level), may be the single best indicator of LDL-associated CHD risk (Lamarche et al., Circulation 1996;94:273-278) and the best target of risk reduction therapy. |
| Low Level of Large HDL | Lower 33% ✓ | Only the larger HDL subclasses appear to be protective, whereas small HDL is positively associated with CHD (Freedman et al., Arterioscler Thromb Vasc Biol. 1998;18:1046-53). Large HDL, rather than total HDL cholesterol, may thus be a more sensitive risk factor. |
| Elevated Level of Large VLDL | Lower 33% ✓ | Elevated levels of large, triglyceride-rich VLDL particles have been associated with CAD severity, independently of plasma triglycerides. High concentrations of large VLDL in fasting plasma may be a marker for delayed chylomicron clearance (postprandial lipemia). |

Subclass Levels

Subclass levels in mg/dL are given in parentheses above each bar. Bar height gives percent of population with lower levels.

VLDL Subclasses (mg/dL Triglyceride): Large VLDL (30), Medium VLDL (74), Small VLDL (4)
LDL Subclasses (mg/dL Cholesterol) (110): IDL (9), Large LDL (31), Medium LDL (15), Small LDL
HDL Subclasses (mg/dL Cholesterol): Large HDL (21), Small HDL (21)

Primary Prevention Risk Assessment — Employs the Framingham algorithm in *Circulation* 1998;97:1837-1847

Given below is the patient's Framingham risk score and the estimated 10-year risk of developing CHD. Also given is the desirable low-level risk for the same age. Risk reduction should focus on modifying the starred risk factors.

Risk Factor Chart

| Risk Factor | Relative Risk | Points |
|---|---|---|
| Age (53) | | 6 |
| * LDL-C (165) | High | 2 |
| * HDL-C (42) | High | 2 |
| Blood Pressure (132/86) | Moderate | 0 |
| Diabetes (No) | Low | 0 |
| * Smoker (Yes) | High | 2 |
| | Point Total | 12 |

Risk of Coronary Heart Disease

| Point Total | 10-Year CHD Risk | Point Total | 10-Year CHD Risk | Point Total | 10-Year CHD Risk |
|---|---|---|---|---|---|
| ≤-2 | 1% | 6 | 6% | 12 | 15% |
| -1,0,1 | 2% | 7 | 7% | 13 | 17% |
| 2 | 3% | 8 | 8% | 14 | 20% |
| 3 | 3% | 9 | 9% | 15 | 24% |
| 4 | 4% | 10 | 11% | 16 | 24% |
| 5 | 5% | 11 | 13% | ≥17 | ≥32% |

Patient's Risk: 15%  Projected Risk at Age 60: 20%
Desirable Risk: 6%   Desirable Risk at Age 60: 8%

Desirable risk is calculated for a non-smoking, non-diabetic woman the same age, with optimal blood pressure (<120/80), LDL cholesterol 100-129 mg/dL, and HDL cholesterol 55 mg/dL. Projected risk at age 60 assumes patient's risk factors do not change.

© LipoScience, Inc. 02/99

FIG. 2

Risk Assessment Report

| Patient Name | Specimen ID | Date Reported |
|---|---|---|
| John Doe | LM99-3201 | 01-27-99 |

Supplemental Risk Factors

CHD risk can increase significantly when there is a clustering of metabolic abnormalities not detected by standard lipid measurements. Check marks in multiple boxes signify the presence of a metabolic profile associated with a higher level of risk than indicated by the LDL cholesterol value.

Small LDL — Pattern B ✓ — Small LDL (Pattern B) is a hallmark of the "atherogenic lipoprotein phenotype" and confers approximately 3-fold higher risk compared to the large LDL trait (Pattern A). Evidence suggests that small LDL particles may be inherently more atherogenic than large LDL.

Elevated Number of LDL Particles — Upper 33% ✓ — Unlike LDL cholesterol, LDL particle concentration (related closely to plasma apo B level), may be the single best indicator of LDL-associated CHD risk (Lamarche et al., Circulation 1998;94:273-278) and the best target of risk reduction therapy.

Low Level of Large HDL — Lower 33% ✓ — Only the larger HDL subclass particles appear to protect against CHD, whereas small HDL may even be atherogenic (Freedman et al., Arterioscler Thromb Vasc Biol. 1998;18:1048-53). Large HDL, rather than total HDL cholesterol, may thus be a more sensitive risk factor.

Elevated Level of Large VLDL — Upper 33% ✓ — Elevated levels of large, triglyceride-rich VLDL particles appear to be associated with CAD severity, independently of plasma triglycerides. High concentrations of large VLDL in fasting plasma may be a marker for delayed chylomicron clearance (postprandial lipemia).

Primary Prevention Risk Assessment

Employs the Framingham algorithm in *Circulation* 1998;97:1837-1847

Given below is the patient's Framingham risk score, the estimated absolute 10-year risk of developing CHD, and the desirable risk level for the same age. Risk reduction should focus on modifying the starred risk factors.

Risk Chart

| Risk Factor | Relative Risk | Points |
|---|---|---|
| Age (46) | | 2 |
| * LDL-C (198) | Very High | 2 |
| * HDL-C (41) | High | 1 |
| * Blood Pressure (135/91) | High | 2 |
| Diabetes (No) | Low | 0 |
| * Smoker (Yes) | High | 2 |
| | Point Total | 9 |

Absolute 10-Year CHD Risk

| Point Total | 10-Year CHD Risk | Point Total | 10-Year CHD Risk |
|---|---|---|---|
| ≤-3 | 1% | 6 | 11% |
| -2 | 2% | 7 | 14% |
| -1 | 2% | 8 | 18% |
| 0 | 3% | 9 | 22% |
| 1 | 4% | 10 | 27% |
| 2 | 4% | 11 | 33% |
| 3 | 5% | 12 | 40% |
| 4 | 7% | 13 | 47% |
| 5 | 9% | ≥14 | ≥56% |

Desirable Risk for Same Age: 4%

The desirable risk is calculated for a non-smoking, non-diabetic man the same age, with optimal blood pressure (<120/80), LDL cholesterol 100-129 mg/dL, and HDL cholesterol 45 mg/dL.

Secondary Prevention Guidelines

Patients with established CHD, other atherosclerotic vascular disease, or diabetes are considered to be at particularly high risk by the NCEP. The primary goal of lipid management should be the reduction of LDL cholesterol to under 100 mg/dL. The corresponding NMR LDL particle concentration target is 1100 nmol/L. For patients with a small LDL (pattern B) and a clustering of the supplemental risk factors shown above, it is especially important to reach these LDL goals. Smoking cessation, increased exercise, healthy diet, and blood pressure control are also important treatment goals.

FIG. 2A

LIPID PROFILE*

| | | Current NCEP Guidelines for Primary Prevention | | |
|---|---|---|---|---|
| Total Cholesterol (mg/dL) | 230 | Desirable: less than 200 | Borderline-High: 200-239 | High: 240 or greater |
| LDL Cholesterol | 165 | Desirable: less than 130 | Borderline-High: 130-159 | High: 160 or greater |
| HDL Cholesterol | 42 | Negative Risk Factor: 60 or greater | Intermediate: 35-59 | Positive Risk Factor: less than 35 |
| Triglycerides | 160 | Desirable: less than 200 | Borderline-High: 200-400 | High: 400-1,000 |

* Lipid profile values are derived from direct NMR measurement of plasma lipoproteins, not from standard lipid tests. For most patients, NMR and standard lipid panel values agree closely. Some patients with metabolic abnormalities or elevated triglycerides have abnormally cholesterol-poor LDL particles. Their LDL cholesterol levels when measured by standard tests will be lower than determined by NMR. The NMR values more closely reflect the actual number of LDL particles in the circulation.

FIG. 3

Supplemental Risk Factors

CHD risk can increase significantly when there is a clustering of metabolic abnormalities not detected by standard lipid tests. A check mark in multiple boxes below suggests the patient has a metabolic profile associated with a higher level of risk.

| | Pattern B | Small LDL (Pattern B) is a hallmark of the "atherogenic lipoprotein phenotype" and confers about 3 to 4-fold higher risk compared to the large LDL trait (Pattern A). Evidence suggests that small LDL particles may be inherently more atherogenic than large LDL. |
|---|---|---|
| Small LDL | ✓ | |

| | Upper 33% | Unlike LDL cholesterol, LDL particle concentration (related closely to plasma apo B level), may be the single best indicator of LDL-associated CHD risk (Lamarche et al., Circulation 1996;94:273-278) and the best target of risk reduction therapy. |
|---|---|---|
| Elevated Number of LDL Particles | ✓ | |

| | Lower 33% | Only the larger HDL subclasses appear to be protective, whereas small HDL is positively associated with CHD (Freedman et al., Arterioscler Thromb Vasc Biol. 1998;18:1046-53). Large HDL, rather than total HDL cholesterol, may thus be a more sensitive risk factor. |
|---|---|---|
| Low Level of Large HDL | ✓ | |

| | Upper 33% | Elevated levels of large, triglyceride-rich VLDL particles have been associated with CAD severity, independently of plasma triglycerides. High concentrations of large VLDL in fasting plasma may be a marker for delayed chylomicron clearance (postprandial lipemia). |
|---|---|---|
| Elevated Level of Large VLDL | ✓ | |

FIG. 5

Primary Prevention Risk Assessment

Employs the Framingham algorithm in *Circulation* 1998;97:1837-1847

Given below is the patient's Framingham risk score and the estimated 10-year risk of devoloping CHD. Also given is the desirable low-level risk for the same age. Risk reduction should focus on modifying the starred risk factors.

Risk Factor Chart

| Risk Factor | Relative Risk | Points |
|---|---|---|
| Age (53) | | 6 |
| * LDL-C (165) | High | 2 |
| * HDL-C (42) | High | 2 |
| Blood Pressure (132/86) | Moderate | 0 |
| Diabetes (No) | Low | 0 |
| * Smoker (Yes) | High | 2 |
| | Point Total | 12 |

Risk of Coronary Heart Disease

| Point Total | 10-Year CHD Risk | Point Total | 10-Year CHD Risk | Point Total | 10-Year CHD Risk |
|---|---|---|---|---|---|
| ≤-2 | 1% | 6 | 6% | 12 | 15% |
| -1,0,1 | 2% | 7 | 7% | 13 | 17% |
| 2 | 3% | 8 | 8% | 14 | 20% |
| 3 | 3% | 9 | 9% | 15 | 24% |
| 4 | 4% | 10 | 11% | 16 | 24% |
| 5 | 5% | 11 | 13% | ≥17 | ≥32% |

Patient's Risk 15%  Projected Risk at Age 60 20%
Desirable Risk 6%  Desirable Risk at Age 60 8%

Desirable risk is calculated for a non-smoking, non-diabetic woman the same age, with optimal blood pressure (<120/80), LDL cholesterol 100-129 mg/dL, and HDL cholesterol 55 mg/dL. Projected risk at age 60 assumes patient's risk factors do not change.

FIG. 7

Positive Risk Factor Chart   Relative Risk   Points
HDL-C ≥ 60                   Negative        -1
LDL Size  Pattern A          Negative        -2
Elevated Large HDL           Negative        -1
Exercise                     Negative        -1

FIG. 7A

Secondary Prevention Guidelines
Patients with established CHD, other atherosclerotic vascular disease, or diabetes are considered to be at particularly high risk by the NCEP. The primary goal of lipid management should be the reduction of LDL cholesterol to under 100 mg/dL. The corresponding NMR LDL particle concentration target is 1100 nmol/L. For patients with small LDL (pattern B) and a clustering of the supplemental risk factors shown above, it is especially important to reach these LDL goals. Smoking cessation, increased exercise, healthy diet, and blood pressure control are also important treatment goals.

METHODS FOR PROVIDING PERSONALIZED LIPOPROTEIN-BASED RISK ASSESSMENTS

RELATED APPLICATIONS

This application is a continuation of U.S. patent application Ser. No. 09/258,740, filed Feb. 26, 1999, now abandoned, the contents of which are hereby incorporated by reference as recited in full herein.

FIELD OF THE INVENTION

The present invention relates generally to reporting and analyzing information related to patient-specific measured lipoprotein results.

BACKGROUND OF THE INVENTION

Recently, a significant advance in measurement techniques used to analyze blood plasma lipoprotein samples was achieved. Lipoproteins are the spherical particles that transport cholesterol, trigylcerides, and other lipids in the bloodstream. The advanced measurement technique employs NMR spectroscopy to provide additional (higher order) increased patient-specific information over the types of information typically provided under routine conventional analysis methods. See U.S. Pat. No. 4,933,844 to Otvos, entitled "Measurement of Blood Lipoprotein Constituents by Analysis of Data Acquired From an NMR Spectrometer" and U.S. Pat. No. 5,343,389 to Otvos, entitled "Method and Apparatus for Measuring Classes and Subclasses of Lipoproteins." The contents of these documents are hereby incorporated by reference as if recited in full herein. Unlike conventional "routine" type laboratory lipoprotein blood tests, the lipoprotein analysis provided by the NMR spectral analysis now more easily provides lipoprotein subclass information, which had, until this advance, been generally inaccessible to clinicians. This subclass information can provide information corresponding to the sizes of the lipoprotein particles that make up a person's lipoprotein constituents.

Lipoprotein subclass information is not part of conventional lipid panels. The conventional panels typically only provided information concerning total cholesterol, triglycerides, low-density lipoprotein (LDL) cholesterol (generally a calculated value), and high-density lipoprotein (HDL) cholesterol. In contrast, the NMR analysis can provide information about (a) the concentrations of six subclasses of very low density lipoprotein (VLDL), four subclasses of LDL (including intermediate-density IDL), and five subclasses of HDL, (b) average LDL particle size (which can be used to categorize individuals into LDL subclass pattern-determined risk), and (c) LDL particle concentration.

The subclass information now available with the NMR spectral analysis can be a more reliable indicator of a patient's risk to develop coronary heart disease. Indeed, recent scientific research has shown that various subclasses of lipoproteins may provide more reliable markers of the metabolic conditions that predispose individuals to a greater or lesser risk of heart disease. However, the NMR spectral analysis can also provide higher-order information about the levels of variously atherogenic or antiatherogenic subclasses that make up each of the major lipoprotein classes.

This subclass information can provide a clear indication about a patient's propensity to develop coronary heart disease. Unfortunately, this additional information can confuse a reviewer as to the meaning of the data, and further, the additional information can be difficult to analyze in a readily discernable manner. For example, a typical NMR lipoprotein analysis can include at least fifteen more values of lipoprotein concentration and size than is provided by standard lipoprotein panels. There is, therefore, a need to analyze and present the lipoprotein-based information in a manner or format which is visually easy to read and understand.

OBJECTS AND SUMMARY OF THE INVENTION

It is therefore an object of the present invention to provide a lipoprotein profile analysis with subclass information with an easily read display format.

It is also an object of the present invention to provide a lipoprotein-based risk assessment which analyzes a patient's measured major lipoprotein constituent values and selected subclass information and presents them in a format in which a patient's specific values are presented in a reader-friendly format.

It is a further object of the present invention to provide a method of generating a custom report at a commercial volume and which can analyze and/or report a patient's risk factors for certain diseases based on NMR spectra of lipoprotein constituents and constituent subclasses.

These and other objects of the present invention are provided by a method for providing and presenting or displaying a customized patient-specific lipid analysis profile with a risk assessment portion for the measured results. In particular, a first aspect of the present invention is directed to a method for providing personalized lipoprotein-based risk assessment information. The method includes the step of generating NMR-based lipoprotein measurement values for a patient's blood plasma or serum sample, the lipoprotein measurement values including at least one subclass variable value. The at least one patient lipoprotein subclass measurement variable value is compared with predetermined test criteria to determine whether the at least one subclass variable value is associated with a higher or lower risk of developing coronary heart disease. The method also identifies what the level of coronary heart disease risk is for the at least one measured subclass variable value. The lipoprotein measurement values are presented in a two-dimensional window such that each of the lipoprotein measurement values are visually enhanced. A risk analysis portion is provided adjacent to the measured lipoprotein values, the risk analysis portion displaying information related to a range of values corresponding to higher and lower coronary heart disease risk. The measured value is visually enhanced in the risk analysis portion to indicate the level of risk associated therewith to thereby provide a contemporaneous reference guideline for interpretation of the measured value. Preferably, the lipoprotein measurement values are presented such that each of the lipoprotein measurement values is substantially vertically aligned and the risk analysis portions are also substantially vertically aligned.

Another aspect of the present invention is directed to a method of presenting NMR derived lipoprotein subclass information in a two-dimensional window. The method includes the steps of obtaining lipoprotein information having a plurality of lipoprotein subclass variable values associated with NMR derived lipoprotein analysis and identifying a risk level associated with coronary heart disease for each of the obtained subclass variable values. The obtained lipoprotein information with subclass values is analyzed to determine the associated risk level. Each of the obtained lipoprotein subclass variable values is arranged in a display format which positions the lipoprotein subclass values adjacent to a corresponding risk analysis portion. The risk analysis portion characterizes the subclass variable value's determined risk level and visually enhances the subclass variable value within the respective risk analysis portion such that the risk associated with the lipoprotein subclass variable value is readily apparent.

An additional aspect of the present invention is an automated lipoprotein report including data corresponding to NMR-derived measurements. The report comprises a first lipid profile segment comprising a plurality of NMR derived major lipoprotein constituent values, each major lipoprotein value having an associated risk analysis portion and a second subclass profile segment comprising a plurality of NMR-derived subclass variables, each subclass variable having an associated risk analysis portion which is configured to visually enhance the risk of developing coronary heart disease for each of said plurality of subclass values, wherein the lipoprotein report is generated at a commercial volume by a computer based on NMR derived patient-specific values.

In a preferred embodiment, each of the major constituent lipoprotein risk analysis portions identifies three risk categories associated therewith. It is also preferred that the risk analysis portion for a plurality of the subclass values is presented as a horizontally extending linear bar graph which graphically represents the subclass value relative to a continuum of low to high risk of developing CHD.

Similar to the above-described aspect, another aspect of the present invention is directed to an automated lipoprotein subclass report which is generated at a commercial laboratory. The subclass report is based on and includes data corresponding to NMR-derived measurements and comprises a subclass profile segment with a plurality of patient-specific NMR derived subclass variables. Each subclass variable has a value and has an adjacently positioned associated risk analysis portion which visually identifies in graphic and verbal form, a risk level associated with the subclass value.

In a preferred embodiment, the lipoprotein subclass report subclass profile segment includes the average of the LDL size. The associated risk analysis portion presents the LDL size as one of three patterns, Pattern A corresponding to lower risk, Pattern B corresponding to higher risk, and Pattern AB corresponding to an intermediate risk. The LDL size classification is identified in the risk analysis portion by visually enhancing the respective pattern associated with the patient-specific LDL size value.

Another aspect of the present invention is directed to computer program products for providing personalized lipoprotein-based risk assessments and reports. The computer program product comprises a computer readable storage medium having computer readable program code means embodied in the medium, the computer-readable program code means comprises computer readable program code means for generating NMR-based lipoprotein measurement values for a patient's blood sample, the lipoprotein measurement values including at least one subclass variable value. The computer program product also includes computer readable program code means for comparing the at least one patient lipoprotein subclass measurement variable value with predetermined test criteria for determining whether the at least one subclass variable value is associated with a higher or lower risk of developing coronary heart disease. The product additionally includes computer readable program code means for identifying, for the at least one measured subclass value, the corresponding risk level associated with coronary heart disease and computer readable program code means for providing a risk analysis portion adjacent the measured lipoprotein values, the risk analysis portion displaying information related to a range of values and corresponding to higher and lower coronary heart disease risk. The risk analysis program code means is configured to present the measured value such that it is visually enhanced in the risk analysis portion to visibly indicate the level of risk associated therewith to thereby provide a contemporaneous reference guideline for interpretation of the measured value.

Another aspect of the present invention is directed to a computer program product for providing a lipoprotein subclass report.

Preferably, for the reports, methods, and computer program products directed to lipoprotein information, the measured lipoprotein values include (a) the major lipoprotein constituents of total cholesterol, LDL cholesterol, HDL cholesterol, and triglycerides and (b) the LDL size and the levels of LDL particles, large HDL cholesterol, and large VLDL triglyceride.

The present invention is advantageous because it provides NMR-derived lipoprotein results with associated risk information in a format that is easy to understand and aesthetically pleasing. Further, the patient's specific subclass profile is presented in the risk assessment report in a graphically enhanced or visually emphasized format so the clinician or layman can easily understand the risk category associated with one or more of a patient's subclass values. Further, the customized report is provided in a computer program product allowing mass or commercial level automated production of a summary report which includes a risk analysis portion which can be customized to report the patient's results in a visually enhanced format.

BRIEF DESCRIPTION OF THE DRAWINGS

FIG. 1 illustrates a lipoprotein summary report according to the present invention.

FIG. 2 illustrates a risk assessment report according to one embodiment of the present invention which may be included in or provided separate from the lipoprotein summary report of FIG. 1.

FIG. 2A illustrates an alternative embodiment of the risk report shown in FIG. 2.

FIG. 3 illustrates a lipid profile segment of the lipoprotein summary report of FIG. 1.

FIG. 5 illustrates a supplemental risk factor segment of the risk assessment report of FIG. 2.

FIG. 7 illustrates a primary prevention risk assessment segment of the risk assessment portion of FIG. 2.

FIG. 7A illustrates a prevention risk assessment segment having positive risk factors identified as negative numbers to be added to negative risk factors having positive numbers such as those shown in FIG. 7 to provide an overall adjusted risk assessment according to the present invention.

FIG. 8 illustrates a secondary risk segment including information regarding high-risk medical conditions for the risk assessment report of FIG. 2A.

DETAILED DESCRIPTION OF THE INVENTION

Figure 4:
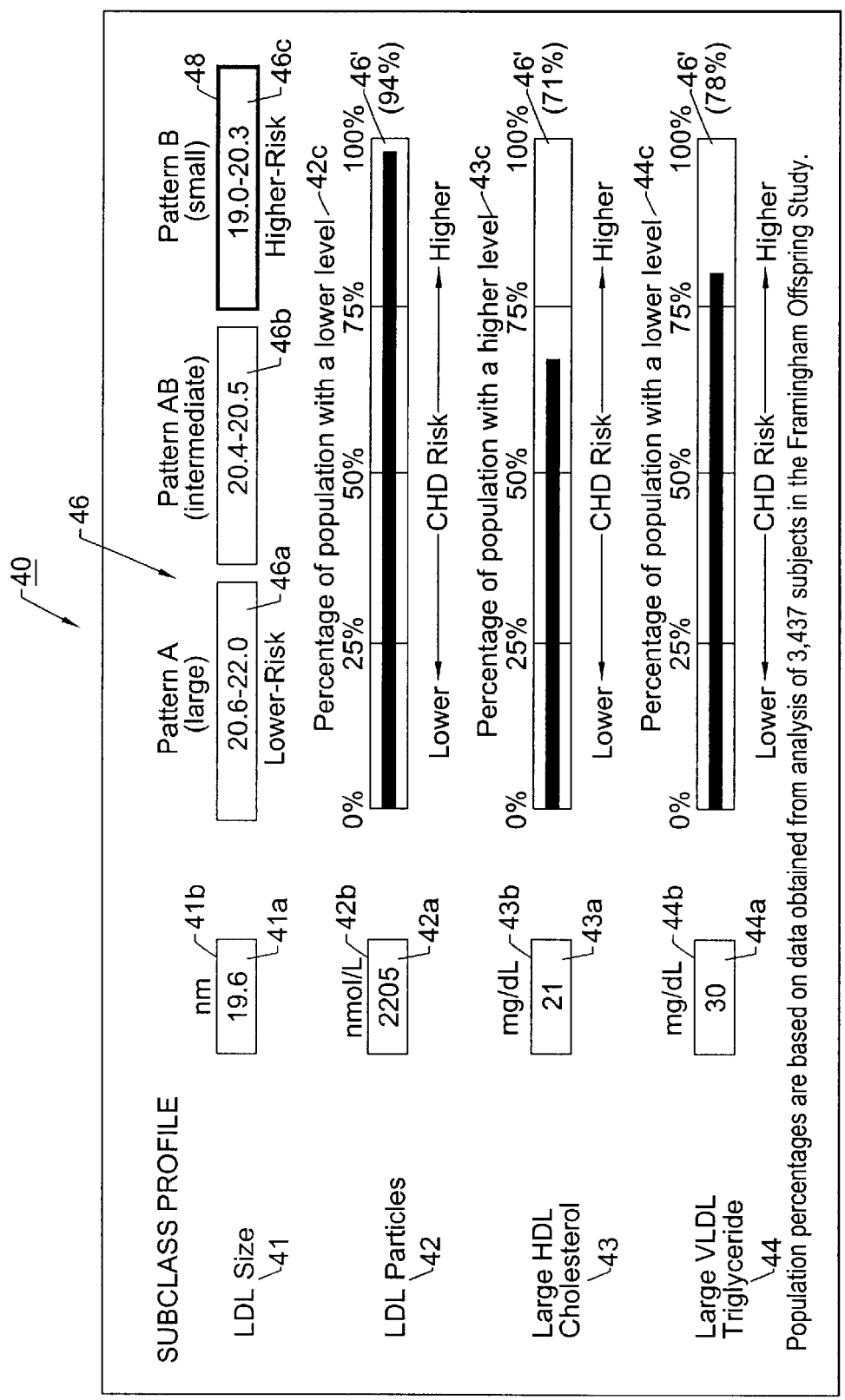
FIG. 4 illustrates a subclass profile segment of the lipoprotein summary report of FIG. 1.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Referring now to FIG. 1, a preferred embodiment of a NMR lipoprotein profile summary report 10 is shown. Preferably, the lipoprotein profile summary report 10 is divided into at least three horizontally oriented segments 20, 30, 40. The first segment 20 of the summary report 10 includes patient identification data 21 such as a name, identification number, and any relevant personal history such as age, smoking status, and other related medical history. As shown, the first segment 20 can also include physician data 22 and a comment section 23. The second segment 30 of the summary report 10 presents the lipid profile analysis and will be discussed further below. The third segment 40 of the summary report 10 presents the subclass profile analysis and will also be discussed further below.

As shown in FIG. 2, the summary report 10 can also include a risk assessment report 10' containing information targeted to a more detailed risk assessment. Of course, the summary report 10 and the risk assessment report 10' as well as individual segments of each can be individually reported, presented or provided. In any event, as shown, the risk assessment report 10' includes a fourth segment 50 which presents supplemental risk factors, and a fifth segment 60 containing individual lipoprotein subclass levels. The summary report 10 can also include an optional sixth segment 70 which can incorporate primary prevention risk assessment information which can predict long term (i.e., 10 year) coronary heart disease (CHD) risk percentages.

As shown in FIG. 2A, a risk assessment report 10" can also include a seventh segment 80 directed to secondary prevention guidelines which can summarize high risk conditions and characterizations, such as atherosclerotic vascular disease and diabetes, and general lipid management goals. This secondary prevention information may be help assist medical personnel in alternative treatment and to alert as to potential high-risk behavior or conditions. As shown, the risk assessment report is rearranged to present the fourth segment 50, the sixth segment 60, and the seventh segment 80. The information in this sample risk assessment report 10" is from a different patient than the results shown in FIGS. 1 and 2.

In a preferred embodiment, the major lipoprotein constituent values and the selected subclass values are generated via the NMR spectral analysis discussed above. The data are typically obtained by processing a blood plasma or serum sample obtained from a subject. As such, as used herein the terms "blood" and "plasma and "serum" sample are interchangeable, as each is suitable for obtaining the desired NMR spectroscopy signal.

Turning now to FIG. 3, a preferred embodiment of the lipid profile or second segment 30 of the summary report 10 is shown. The patient-specific lipid value results of total cholesterol 31, LDL cholesterol 32, HDL cholesterol 33, and triglycerides 34 are listed and arranged in aligned order from a top portion 30a of the second segment to a bottom portion 30b of the second segment. Preferably, alongside the listed order of the total cholesterol, LDL, HDL, and triglycerides, 31, 32, 33, and 34, respectively, the associated actual measured values 31a, 32a, 33a, and 34a are also serially aligned. Preferably, the values 31a, 32a, 33a, 34a are each displayed in a box 31b, 32b, 33b, 34b. Of course, the values 31a, 32a, 33a, and 34a may otherwise be presented, but are preferably presented in a visually enhanced format (such as via bold, italics, shaded, font (size, type), circled, underlined, colored or highlighted by other visual enhancement means) to provide ready visual recognition of the patient-specific results.

As is also shown in FIG. 3, the second segment 30 also preferably includes risk assessment guidelines 35 which represent a relative reference, guideline, or "yardstick" of the patient's value as compared to targeted values. Preferably, the risk assessment guidelines 35 divide the respective measured patient value for each of the total cholesterol 31, LDL 32, HDL 33, and triglycerides 34 into three different categories 36 of risk associated with a predetermine range of values (shown as measured in mg/dL). These predetermined range of values are based on predetermined test criteria.

As shown, the three categories for total cholesterol 31 and LDL 32 are labeled desirable 36a, borderline-high 36b, and high 36c. As shown, for total cholesterol 31, the desirable 36a category is defined as a value less than 200. For LDL 32, the desirable category 36a, is defined as a value less than 130. The borderline-high category 36b is defined as a range of values between 200–239 for total cholesterol 31 and between 130–159 for LDL 32. The high category 36c is defined as 240 or greater for total cholesterol 31 and 160 or greater for LDL 32.

Referring again to FIG. 3, the HDL categories 36 are labeled as negative risk factor 36d, intermediate 36e, and positive risk factor 36f. The negative risk factor 36d is defined as a value of 60 or greater, the intermediate risk category 36e is defined as a value between and including 35–59, and the positive risk factor 36f is defined as a value less than 35.

The triglycerides categories 36 are labeled as normal 36g, borderline-high 36h, and high 36i. The normal category 36g is defined as a triglyderides value 33 of less than 200, the a borderline-high category 36h is defined a value between 200–400, and the high category 36i is defined as a value greater than 400 (but typically below 1000).

Preferably, the predetermined test criteria or targeted or ranges of values associated with each category of risk 36a–36i are defined to correspond to current National Cholesterol Education Program (NCEP) guidelines for primary prevention of coronary heart disease. See National Cholesterol Education Program, *Second Report of the Expert Panel on Detection, Evaluation, and Treatment of High Blood Cholesterol in Adults (Adult Treatment Panel II)*, Circulation 1994; 89:1329–1445. Of course, other suitable values or definitions can also be used, such as population based norms or other targeted based norms.

Preferably, as shown in FIGS. 1 and 3, the risk category 36 which corresponds to the patient value is visibly enhanced so that a reader can readily discern the category associated with the patient specific result (i.e., a visually enhanced risk category 38). For example, a person reviewing the patient-specific results shown in FIG. 3 can readily discern that the patient results indicate that the patient is "high risk" in one category (LDL cholesterol 32), intermediate/borderline in two categories (cholesterol 31 and HDL cholesterol 33), and desirable in the other category (triglycerides 34). Further, a reviewer could readily discern how close the measured value is to the next adjacent risk category for each value 31, 32, 33, 34, which can also facilitate a more complete understanding of the results.

Preferably, as shown, the risk assessment 35 is formatted so that the three risk categories 36 for each measured value are similarly sized and configured and are arranged serially over or under the adjacent measured value. In this way, each of the categories 36 for each measured value is positionally vertically aligned. The "low" or "negative/good" risk values 36a, 36d, 36g are positioned on one edge of a risk bar 36' and the "high" or "bad/positive" risk values 36c, 36f, 36i are positioned at the opposing edge of the risk bar 36'. This presentation yields an aesthetic, easily readable format and informational horizontal continuum of risk characterization associated with the patient's results. As is also shown, the summary report 10 (or one or more of the segments 20, 30, 40) can include a descriptive comment portion 39 which discusses slight differences which may be observed from NMR spectral measurements compared to conventional or standard tests.

Turning now to FIG. 4, a preferred embodiment of the third segment 40 of the summary report 10 presenting the subclass profile is shown. The third segment 40 preferably includes four measured subclass variables, the subclass variables being labeled as LDL size 41, LDL particles 42, large HDL cholesterol 43, and large VLDL triglyceride 44. The LDL size value 41a is shown as measured in nanometers (nm). The LDL particles value 42a is shown as measured in nano-moles per liter (nmol/L) while the large HDL cholesterol value 43a and the large VLDL triglyceride value 44a are measured in milligrams per deciliter (mg/dL).

As for the lipid profile results discussed for the second segment 30 above, each of the measured values 41a, 42a, 43a, 44a are preferably presented in a visually enhanced manner 41b, 42b, 43b, 44b (the results are shown as visually enhanced or offset by a frame or box).

In a preferred embodiment, the third segment 40 also includes a risk assessment portion 46 where the measured results 41a, 42a, 43a, and 44a are visually enhanced and related or compared to predetermined criteria or values. For example, the LDL size result 41a is associated with three risk categories 46a, 46b, 46c. The risk categories 46a, 46b, 46c are defined by a pattern (A, AB, or B, respectively) associated with the particle size. The first category 46a is Pattern A, which is defined as a lower risk pattern associated with large particle sizes of 20.6–22.0. The second category 46b is Pattern AD which is defined as an intermediate risk and corresponds to a particle size of 20.4–20.5. The third risk category 46c is Pattern B and is defined as a higher-risk category and corresponds to smaller particle sizes of between 19.0–20.3.

As shown, the remaining subclass measured values 42a, 43a, 44a, are displayed on a horizontally oriented line graph 46'. Preferably, each line graph 46' plots the patient's results to illustrate whether the result indicates a higher or lower risk of CHD. In the embodiment shown, the graph is used to compare the patient measured result against a percentage of the general population having higher or lower levels of the measured value. Preferably, as shown, the line graphs 46' are plotted such that the results show a greater risk aligned at the right edge of the graph 46'. Stated differently, whether a higher or lower value indicates a higher risk of CHD, each of the line graphs 46' are defined to present the measured value such that the higher risk of CHD is at the same edge of the line graph and the higher and lower risks are thus visually aligned.

For example, the LDL particles 42a and the large VLDL triglyceride values 44a are graphed corresponding to percentage of the population having lower values 42c, 44c while the large HDL value 43a is graphed corresponding to the percentage of population having a higher value 43c. Nonetheless, as shown, the line graphs 46' are oriented and plotted such that the higher risk of CHD is aligned along the right end portion of the line graph. As shown, the patient results illustrate that 94% of the population has a lower LDL particle value 42a, 71% of the population has a higher large HDL value 43a, and 78% of the population has a lower large VLDL triglyceride 44a level.

In a preferred embodiment, the population values are based on scientific results obtained from subjects in the Framingham Offspring Study. See Wilson et al., *Impact of National Guidelines for Cholesterol Risk Factor Screening. The Framingham Offspring Study*, JAMA, 1989; 262: 41–44. Of course the values presently defined for the risk assessment 36, 46 portion of the summary may change over time and more or alternate risk categories may be added. Further, the actual ranges or definitions associated with the risk category values of one or more of the lipid panels or subclass categories may change over time and the present invention is not intended to be limited thereto.

The order of the measured values 31a, 32a, 33a, 34a, 41a, 42a, 43a, and 44a may be alternately arranged in the summary report 10. In addition, the layout of the results may be alternately oriented (such as in vertical segments). Of course, the second segment 30 (lipid profile) or the third segment 40 (subclass profile) may be provided alone depending on a customer's specifications.

It is also preferred that the report include a discussion of "flagged" or potential increased risk factors identified by the subclass values 41a, 42a, 43a, 44a as compared to predetermined risk assessment criteria. For example, as shown in FIG. 5, a supplemental risk factor segment 50 can be included in the summary report 10'. The supplemental segment can include a preliminary informational introduction 50a which notes that coronary heart disease risk can significantly increase when there is a clustering of metabolic abnormalities not detected by standard lipid measurements. The supplemental risk segment 50 summarizes the presence of a metabolic profile associated with a higher level of risk than indicated by the LDL cholesterol value 32a. In a preferred embodiment, the "clustering" is indicated by a mark 51a, 52a, 53a, 54a in a corresponding subclass box 51b, 52b, 53b, 54b.

As shown, this supplemental risk factor segment 50 includes a summary 50' for subclass values indicating abnormalities which indicate increased risk, i.e., Pattern B small LDL 51, elevated number of LDL particles 52, low level of large HDL 53, and elevated level of large VLDL 54. As shown, if the summary 50' is selected (shown as positive with a "check mark" proximate to the category), then the CHD risk is increased. An informational guideline 51c, 52c, 53c, 54c, for the abnormal values is positioned proximate to the subclass box.

In an alternative embodiment (not shown), a computer program can be configured to provide the analysis and risk assessment in a manner in which it can suppress non-abnormal results and provide only abnormal results in this segment 50'. Thus, if a patient has two "abnormal" or elevated risk values associated with the subclass readings, then only those two subclasses will be printed on this segment 50 of the summary report 10.

In any event, as indicated for the small LDL variable 51, small LDL size (Pattern B) is a hallmark of the "atherogenic lipoprotein phenotype" and confers approximately a three-fold higher risk compared to the large LDL trait (Pattern A). There is evidence that suggests that small LDL particles may be inherently more atherogenic than large LDL. As regards an elevated number of LDL particles 52 (shown as for a value corresponding to the upper 33% of the population), unlike LDL cholesterol, LDL particle concentration (related closely to plasma apo B level), may be the single best indicator of LDL-associated CHD risk and the best target of risk reduction therapy. See Lamarche et al., Circulation 1996; 94:273–278. The supplemental risk factor segment 50 can also indicate the presence of low levels of large HDL 43. Low levels of large HDL 43 (shown as a value corresponding to the lower 33% of the population) may be a positive risk factor, as only larger HDL subclass particles appear to protect against CHD—whereas small HDL may even be atherogenic. Therefore, large HDL, rather than total HDL cholesterol, may be a more sensitive risk factor. See Freedman et al., Arterioscler. Thromb. Vasc. Biol. 1998; 18:1046–53. Similarly, as shown, elevated levels of large triglyceride rich VLDL particles 54, appear to be associated with coronary artery disease (CAD) severity, substantially independent of plasma triglycerides. High concentrations of large VLDL in fasting plasma may be a marker for delayed chylomicron clearance (postprandial lipemia).

Figure 6:
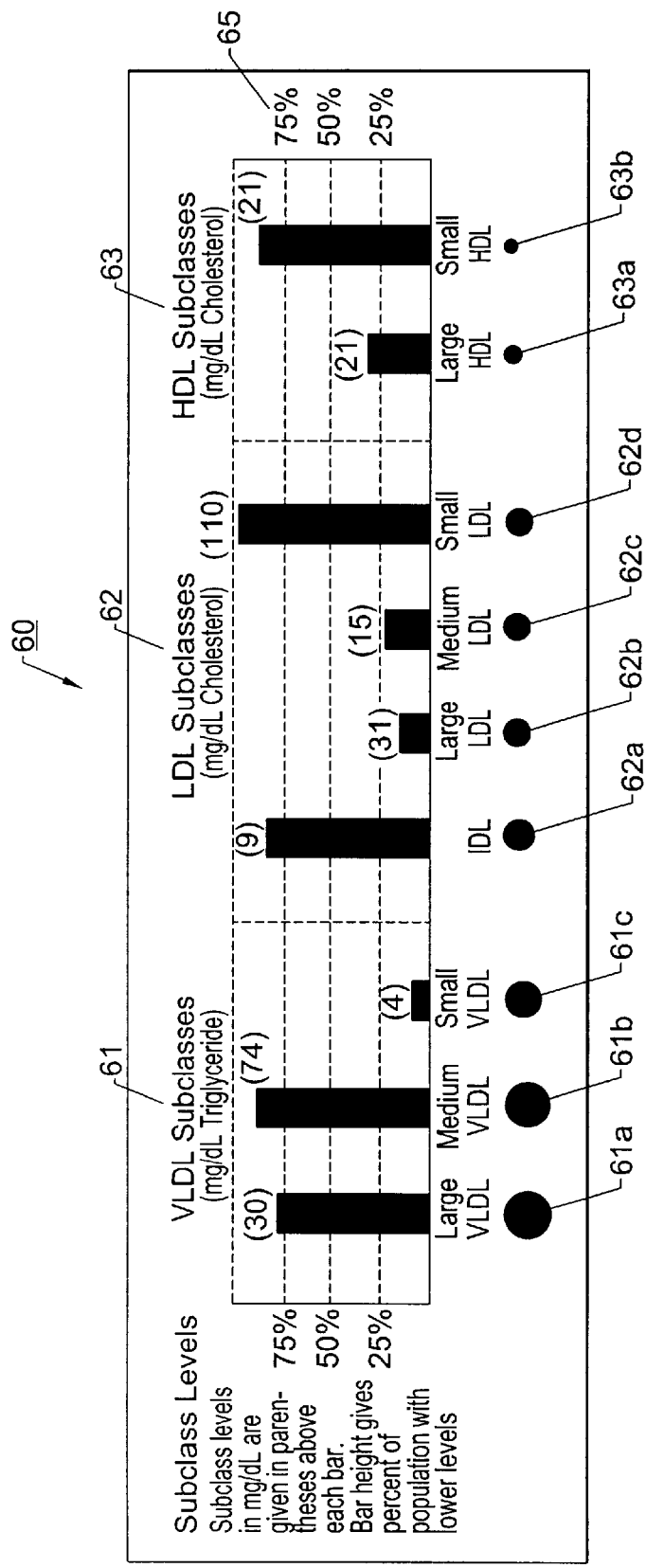
FIG. 6 illustrates a subclass level risk assessment segment for the risk assessment report of FIG. 2.

As shown in FIGS. 2 and 6, the summary report 10 may also include a fifth segment 60 showing a graphical representation of the subclass levels provided by NMR analysis. Referring to FIG. 6, the fifth segment 60 divides the information into three groups of subclasses, VLDL triglyceride subclasses 61, LDL cholesterol subclasses 62, and HDL cholesterol subclasses 63. Each of the three subclasses 61, 62, 63 are further divided to graphically portray selected or grouped results. As shown, the VLDL triglyceride subclass 61 is divided into three groupings, a large VLDL subclass 61a (shown with a concentration or value of 30), a medium VLDL subclass 61b (shown with a value of 74), and a small VLDL subclass 61c (shown with a value of 4). The LDL subclasses 62 shown in FIG. 6 include an IDL cholesterol subclass 62a (shown with a value of 9), a large LDL cholesterol subclass 62b (shown with a value of 31), a medium LDL cholesterol subclass 62c (shown with a value of 15), and a small LDL cholesterol subclass 62d (shown with a value of 110). The HDL subclasses shown are large HDL cholesterol 63a (shown with a value of 21) and small HDL 63b (shown with a value of 21 For each subclass level shown 61a–c, 62a–d, 63a–b, the level measured in mg/dL are provided in text form at the top of the respective bar. The height of the bar gives the percent of population with lower levels of the graphed value. Advantageously, the HDL cholesterol subclass grouping can visually indicate the breakdown of the constituents of the overall HDL class 33 (value 42) shown on the summary report 10 to indicate the correspondence between the two subclasses to the overall HDL number. As shown, the results indicate an even amount of small HDL cholesterol 63b versus large HDL cholesterol 63a. Of course, other groupings or different subclass information may be separated out such as the separable subclass information shown in FIG. 9, as will be discussed further below.

The risk assessment report 10' may also include a sixth segment 70 addressing the primary prevention risk assessment for an individual. Referring to FIG. 7, the sixth segment 70 incorporates certain behavioral and medical background of an individual with the lipid profile and subclass values. For example, a patient's age, smoking history, blood pressure, LDL value 32 and HDL value 33, and whether he or she has diabetes, and/or other risk pertinent information such as whether a blood relative has diabetes or CHD. A risk factor value is assigned to each of these parameters. Additionally, positive risk factors can be assigned a negative risk value (FIG. 7A). Examples of positive risk factors include whether the patient actively exercises at least three days per week, has a high HDL cholesterol level 33a, has a Pattern A LDL size 41a, and has elevated levels of large HDL 43a). The positive and negative risk factors can be added to yield an overall risk value. In any event, a percentage based predictive CHD risk is generated corresponding to the total calculated risk. A target norm for the patient's age and gender can also be provided. In a preferred embodiment, the relative "negative" risk factors and predictive analysis is generated as described by Wilson et al., in *Prediction of Coronary Heart Disease Using Risk Factor Categories,* May 12, 1998 (copyright 1998 American Heart Association, Inc.).

As also shown in FIG. 7, the risk of coronary heart disease is presented in several different percentage-based risk evaluations. A first risk 76a is as indicated by the risk point total. A second risk 76b is a "desirable risk", i.e. the risk associated a non-smoking, non-diabetic person of the same gender and age having optimal blood pressure (less than 120/80), LDL cholesterol of 100–129 mg/dL, and HDL cholesterol of 55 mg/dL. A third risk 76c is a "projected" risk to provide an age accounting balancing of risk (age typically being the single largest risk contributor as indicated in the risk factor chart). Thus, the third risk 76c evaluation can help provide a helpful basis for managed care assessment. A fourth risk 76d can also be included to provide a desirable risk at age 60 (one indicative of only age-related risk conditions). The age standard for persons under the 60 year mark can establish a more clear assessment of the risk a person with the measured values has for coronary heart disease. Advantageously, a patient may take more immediate steps to attempt to reduce the indicated exposure risk when presented with a longer-term standard reference risk.

The summary report 10" may also include a seventh segment 80 which is directed toward secondary prevention guidelines. As shown in FIG. 8, the sixth segment presents a discussion 80a on special risk considerations for patients with established coronary heart disease, other atherosclerotic vascular disease, or diabetes. These patients are considered to be at particularly high risk as measured by the NCEP guidelines. For patients having one or more of these conditions, the present recommendations are lipid management to reduce LDL cholesterol to under 100 mg/dL. The corresponding NMR LDL particle concentration target is 1100 nmol/L. For patients with small LDL (Pattern B) and a clustering of the supplemental risk factors 50 discussed above, it can be especially important to reach these LDL goals. Smoking cessation, increased exercise, healthy diet, and blood pressure control can also be considered important treatment goals.

Figure 9:
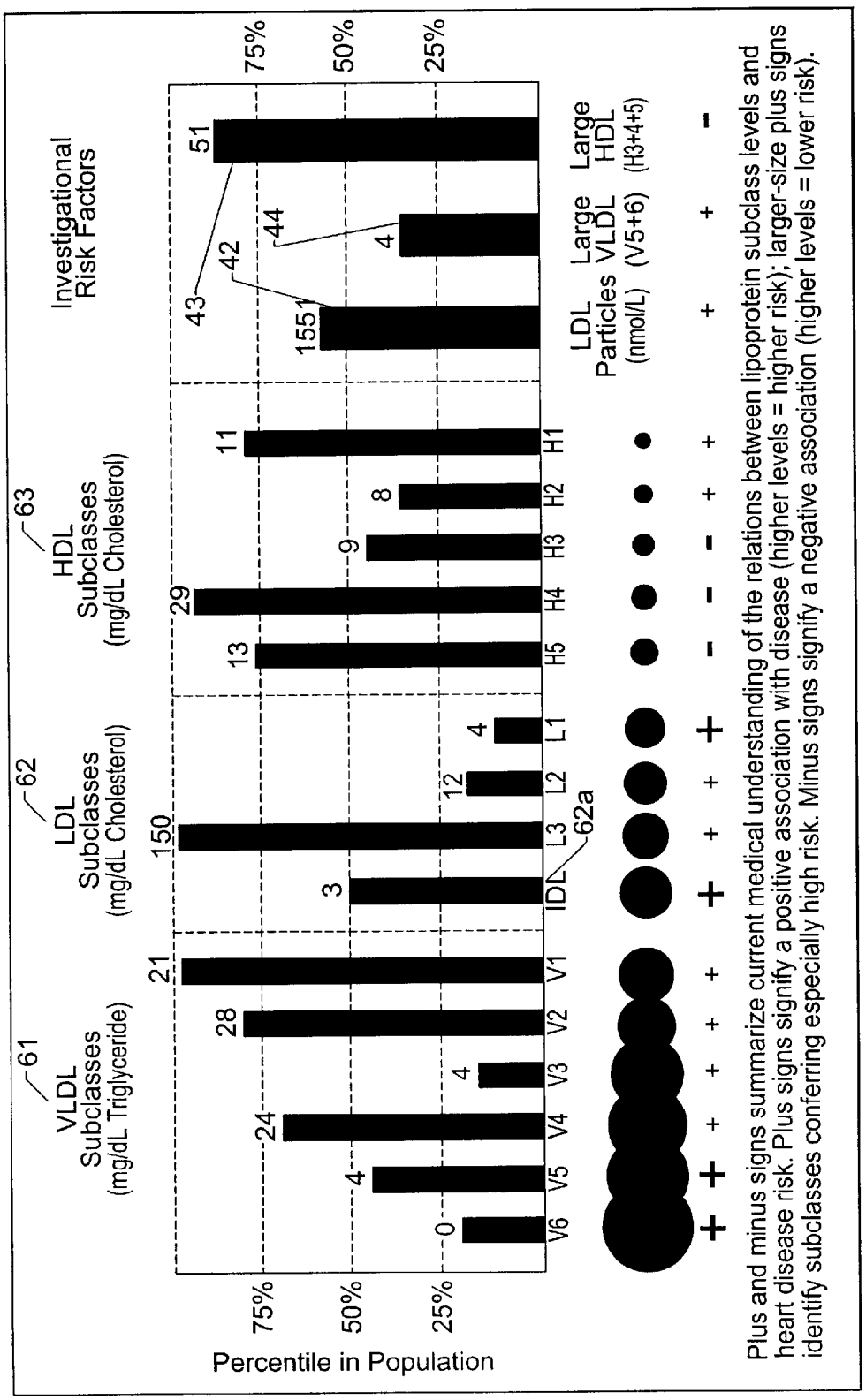
FIG. 9 is a graphic illustration of alternative embodiment of subclass information and associated positive or negative risk with coronary heart disease.

FIG. 9 graphically illustrates some of the subclass information provided by NMR analysis according to the present invention. This graph also shows the present medical understanding of the relationship between various lipoprotein subclass levels and CHD risk. The plus signs represent a positive association with disease (larger size signs indicating subclasses conferring higher risk). The higher levels indicating a higher risk. The minus signs represent a negative association, higher levels equals a lower risk. In a preferred embodiment, certain of the individual subclass information shown is combined with other subclass information shown to provide the subclass groupings described above for FIG. 6.

As discussed above, a preferred embodiment of the summary report 10 includes portions of the subclass information shown in FIG. 8 (42, 43, 44) and also includes LDL size 41. Of course, the summary report 10 can include other subclass information within the scope of this invention. Advantageously, the instant reporting system and product can be used to provide important patient-specific information in an easy to assess manner and can be generated on a mass commercial production basis. Of course, some or part of this information may be presented in a computer readable medium or hard or paper report.

Figure 10:
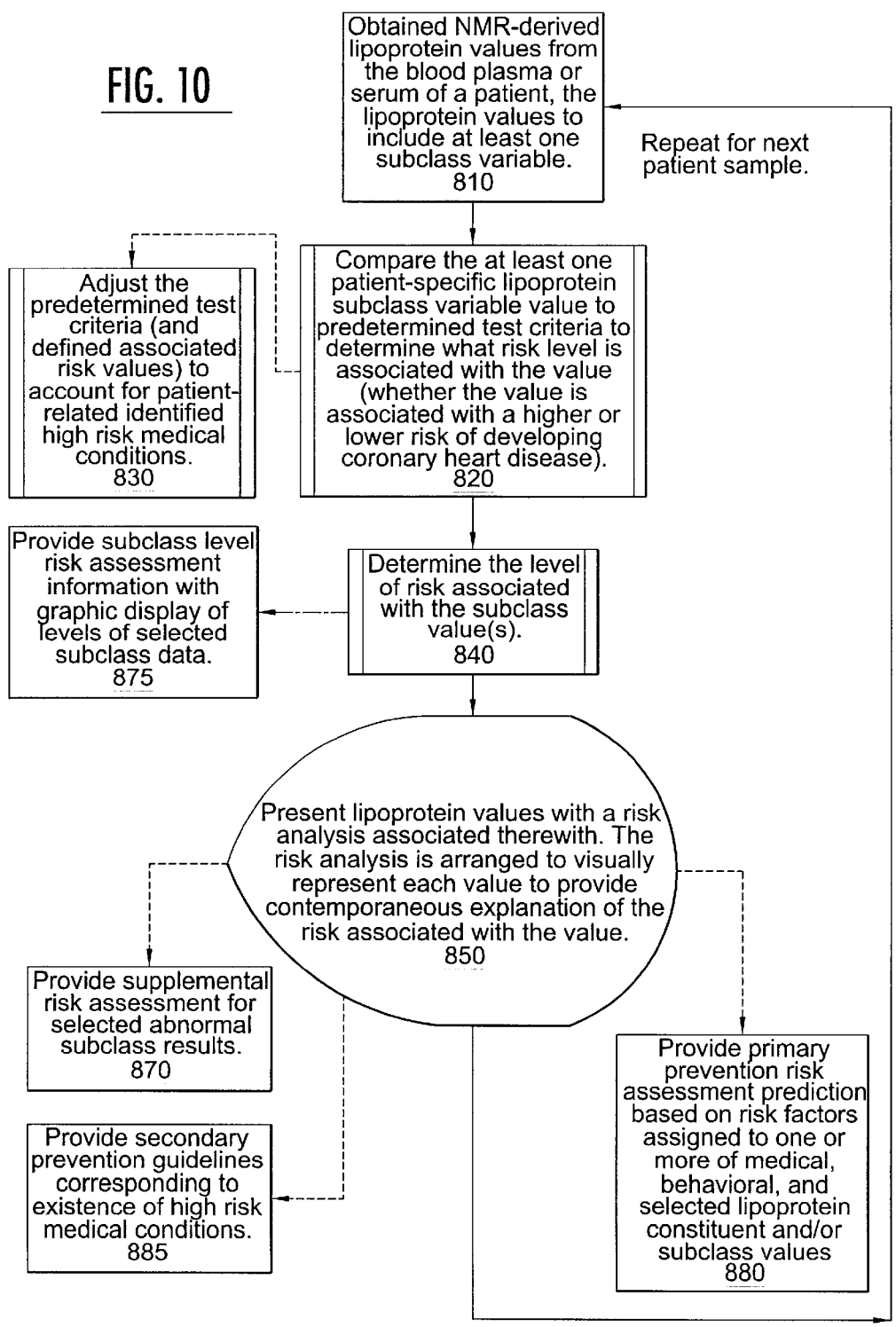
FIG. 10 is a flow chart of a method which analyzes and presents NMR derived lipoprotein information according to the present invention.

FIG. 10 illustrates a flow chart of methods, apparatus (systems) and computer program products according to the invention. It will be understood that each block of the flowchart illustration, and combinations of blocks in the flowchart illustrations, can be implemented by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce computer implemented process such that the instructions which execute on the computer or other programmable apparatus provide steps for implementing the functions specified in the flowchart block or blocks.

Accordingly, blocks of the flowchart illustrations support combinations of means for performing the specified functions and program instruction means for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer instructions.

As shown in FIG. 10, lipoprotein measurement values are obtained from a patient or subject, the values include at least one subclass value (Block 810). Preferably, an NMR spectral analysis is performed on a blood plasma sample and the lipoprotein values measured include the major lipoprotein constituents (total cholesterol, HDL, LDL, and triglycerides) as well as selected subclass values. The patient specific at least one subclass value is compared to predetermined test criteria to determine whether the value is associated with a higher or lower risk of developing coronary heart disease (Block 820). Preferably, the test criteria employed for the lipoprotein results (including the lipoprotein subclass values) correspond to a defined level of risk (low to high) of developing CHD. Preferably, the predetermined test criteria are based on scientific target "norms" or population based norms associated with higher or lower risks of CHD. These values may change over time or can be alternately identified for patients with increased secondary risk factors.

For example, if a patient has established CHD, atherosclerotic vascular disease, and/or diabetes, the "risk" criteria and values of certain constituents or subclasses may be lowered on the summary report relative to a patient without said identified diseases such that a "high" risk value may be associated with a lower value (optional Block 830). This report's ability to automatically adjust or lower the risk value based on preexisting conditions can help alert the physician that this patient is subject to stricter lipid management or protocol by visually indicating the lower risk factor value targeted for this individual. Generally, the test criteria may be set in a controlled revision software format which can be updated as NCEP guidelines or current medical analysis updates risk related information or values.

As shown in FIG. 10, the next step is to determine the level of risk associated with the lipoprotein subclass value(s) (i.e., whether it is identified as being associated with increased-risk (and/or reduced-risk) of developing coronary heart disease) (Block 840). The NMR spectroscopy measured lipoprotein results are presented with a risk category associated with the measured result visually enhanced in a two-dimensional window for easy recognition thereof (Block 850). The two-dimensional window can be a display section on a computer screen, display monitor, or electronic or hard copy or a commercial report portion or segment. Advantageously, the customized display or report can be automatically generated or mass produced such as at a commercial facility or laboratory. As shown in FIG. 1, it is preferred that each of the risk analysis information associated with the measured value be presented such that the "high" or elevated risk information is visually enhanced and aligned along one side (the same side as the other risk information for the other values) of the report or display.

Optionally, as indicated by Blocks 870, 875, 880 and 885, additional risk assessment information can also be provided. For example, a supplemental risk assessment for selected abnormal or higher risk subclass results can be provided (Block 870). This supplemental risk assessment can customize the report to provide more detailed information regarding selected subclass variables (such as LDL size or particles, large HDL, and/or large VLDL triglycerides). Similarly, a subclass level risk assessment can provide a graphic and textual breakdown of certain subclass groupings or selected subclass data (Block 875).

Alternatively, or additionally, a primary prevention risk assessment prediction assessment can be provided based on risk factors assigned to one or more of behavioral, medical, and/or selected lipoprotein measured constituent and/or subclass values (Block 880). As another alternative or addition, a secondary prevention guideline corresponding to recognition of the patient's diagnosis with certain high-risk medical conditions can be provided (Block 885).

Preferably, the method of the instant invention subdivides the major lipoprotein constituents and the LDL pattern separately into at least three risk categories each. It is also preferred that, the LDL particles 42, the large HDL value 43 and the large VLDL triglyceride value 44 are compared to a population based-norm and a line graph illustrates the actual measured result compared to the population with higher or lower levels of the measured value.

The behavioral or medical input can be electronically input or input via a user at the lab or report site (for example, at a blood depository or lab where the blood or plasma sample is taken from a patient). It is typical that an identification number (bar-coded) is assigned to the vials for tracking. Accordingly, a hard copy or electronic data can also be identified such as with the same identification number. Once received at the central processing facility or NMR spectroscopy laboratory, the electronic data can be entered into the facility computer and matched with the lipoprotein measurements, and a customized patient profile summary report can be conveniently generated (either in one or more of soft or hard copy). In one embodiment, the summary report can be encrypted and emailed in electronic format to a physician's address for contemporaneous data reporting. Of course, the patient can be identified by a "permanent" number to track trend or drug therapy or other treatment impact over time. Additionally, a data base can be kept to analyze population trends (age, location, etc., versus one or more of the identified risk factors represented by a subclass and/or constituents) to provide important indicators of the population for medical use.

As will be appreciated by one of skill in the art, the present invention may be embodied as a method, data processing system, hard copy report or program product. Accordingly, the present invention may take the form of an entirely hardware embodiment, an entirely software embodiment or an embodiment which combines software and hardware aspects. Furthermore, the present invention may take the form of a computer program product on a computer readable storage medium having computer readable program code means embodied in the medium. Any suitable computer readable medium may be utilized including for example, hard disks, CD-ROMs, optical storage devices, or magnetic storage devices.

A portion of the disclosure of this patent document contains material which is subject to copyright protection. The copyright owner, LipoScience, Inc., of (Raleigh, N.C., has no objection to the facsimile by anyone of the patent document or the patent disclosure, as it appears in the Patent and Trademark Office patent file or records, but otherwise reserves all rights whatsoever.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. A method for assessing a patient's risk of having or developing coronary heart disease based on lipoprotein measurements, comprising:

generating NMR spectra of a blood plasma or serum sample of a patient;

measuring the values of a plurality of selected lipoprotein subclass constituents in the sample from NMR data;

analyzing the measured values of the lipoprotein subclass constituents according to predetermined test criteria to identify whether there is an increased and/or decreased risk of having and/or developing coronary heart disease associated with the measured lipoprotein subclass constituent values;

outputting the measured lipoprotein subclass values onto a report;

providing a plurality of risk analysis portions, a respective one for each selected measured lipoprotein subclass value, each risk analysis portion depicting the identified risk for the corresponding measured lipoprotein subclass constituents value based on the predetermined test criteria analysis, to provide a contemporaneous risk assessment guide useful for interpretation of the risk associated with the measured value;

automatically adjusting the predetermined risk criteria used to define whether a patient has an increased risk of having or developing coronary heart disease relative to the general population, for at least one selected lipoprotein subclass constituent when the patient has a known or diagnosed selected medical condition to thereby provide at least one reduced lipoprotein therapeutic target value for at-risk patients; and assigning an electronic identifier to a patient and electronically storing and comparing the measured lipoprotein subclass values of the patient over time in an automated manner, to monitor the impact of a drug therapy or treatment thereon.

2. A method according to claim 1, wherein each risk analysis portion defines a plurality of risk segments associated with differing risks from lower risk to higher risk;

positioning the respective risk analysis portions in the report adjacent its measured corresponding lipoprotein subclass value; and drawing a perimeter line associated with a respective one of the risk segments in each risk analysis portion on the report so that it has an increased size, intensity and/or contrasting color for the risk segment associated with the measured lipoprotein subclass value relative to the non-associated risk segments for each risk analysis portion to visually enhance the identified risk.

3. A method according to claim 1, further comprising drawing a box in red in the risk analysis portions for each of the lipoprotein subclass constituent measured values identified as having an increased risk.

4. A method according to claim 1, wherein the plurality of selected lipoprotein subclass constituents include LDL particle concentration, LDL particle size, large HDL, and large VLDL.

5. A method according to claim 4, further comprising drawing a plurality of discrete boxes on the report in the risk analysis portions one for each measured lipoprotein subclass value and drawing the box so tat it has an increased size, intensity and/or contrasting color for the lipoprotein values associated with an increased risk relative to the lipoprotein values not having an increased risk to visually enhance the identified risk.

6. A method according to claim 5, wherein a plurality of the measured lipoprotein subclass constituent risk analysis portions include at least three discrete risk segments defined by rectangular boxes that are horizontally spaced apart in side by side alignment on the report, and wherein the boxes that enclose the measured values are located along the left side portion of the report with the risk analysis portions located centrally and/or to the right side portion of the report.

7. A method according to claim 5, wherein the boxes enclosing the measured values are vertically spaced apart and aligned along the left side portion of the report.

8. A method according to claim 1, wherein each risk analysis portion defines a plurality of risk segments associated with differing risks from lower risk to higher risk, the method further comprising:
drawing a plurality of horizontally spaced apart discrete boxes, one for each risk segment in the risk analysis portions; and
providing a numerical value or range of values in each risk segment box, wherein the perimeter line of the risk segment associated with the identified risk of the measured lipoprotein subclass value is a box line having an increased line density and a contrasting color with respect to the boxes for the remainder of the risk segments in the respective risk analysis portions that are not associated with the identified risk of the measured lipoprotein subclass value.

9. A method according to claim 8, wherein the risk segment boxes are rectangles.

10. A method according to claim 1, further comprising successively repeating the generating, measuring, analyzing, outputting, providing, adjusting and assigning steps for a plurality of different patient samples to thereby successively generate customized NMR-based lipoprotein risk assessments.

11. A method according to claim 1, wherein the generating and measuring steps are carried out to provide measured lipoprotein values of the levels of the major lipoprotein constituents of total cholesterol, LDL cholesterol, HDL cholesterol, and triglycerides, as well as the measured lipoprotein subclass values of the size and/or concentration of ILL particles, the level of large HDL cholesterol, and the level of large VLDL triglyceride, and wherein the analyzing, outputting, providing, and drawing steps are carried out to analyze and report the risk associated with both the major and subclass lipoprotein constituents.

12. A method according to claim 1, further comprising graphing a plurality of subconstituents and/or selected measured lipoprotein subclass values on a bar chart illustrating the percent of the general population having equal or lower levels of that lipoprotein subclass value and depicting the graphs in the report.

13. A method according to claim 1, further comprising drawing, in at least one risk analysis portion, a horizontally extending line graph displaying a lower risk to higher risk continuum such that the horizontally extending line graph is substantially vertically aligned and positioned to the right of the corresponding measured lipoprotein subclass variable value in the report.

14. A method according to claim 1, further comprising electronically transmitting the report to the clinician over a computer network.

15. A method for assessing a patient's risk of having or developing coronary heart disease based on lipoprotein measurements, comprising:
obtaining NMR-derived measured values of selected lipoproteins including a plurality of lipoprotein subclass constituents in a blood plasma or serum sample of a patient;
analyzing the measured values of the selected lipoproteins including a plurality of the lipoprotein subclass constituents according to predetermined test criteria to identify when there is an increased and/or decreased risk of having and/or developing coronary heart disease associated with the measured values;
outputting the measured lipoprotein values onto a report;
providing a plurality of risk analysis portions that depicts the identified risk of the measured lipoprotein and lipoprotein subclass values from the predetermined test criteria analysis, a respective one for each selected measured lipoprotein and lipoprotein subclass value, wherein each risk segment is associated with predetermined ranges of measured numerical values according to the predetermined test criteria;
positioning the respective risk analysis portions in the report adjacent its measured corresponding lipoprotein or lipoprotein subclass value to provide a contemporaneous risk assessment guide useful for interpretation of the risk associated with the measured values; and
calculating reduced values in the predetermined risk criteria associated with a increased risk of having or developing coronary heart disease for selected lipoprotein and/or lipoprotein subclass values relative to the general population when the patient has a known or diagnosed selected at-risk medical condition to thereby provide at least one reduced lipoprotein therapeutic target value for at risk patients; and
assigning an electronic identifier to a patient and electronically storing and comparing over time in an automated manner, the measured lipoprotein subclass values of the patient to monitor the impact of a drug therapy or treatment thereon.

16. A method according to claim 15, wherein each risk analysis portion defines a plurality of risk segments that are associated with different degrees of risk from decreased risk to increased risk, the method further comprising drawing for a plurality of the risk analysis portions on the report, a box with a perimeter line being adjustable to present the line of the risk segment box associated with the measured value with a contrasting color to visually enhance the identified risk, wherein the drawing is carried out so that the perimeter line of the risk segments associated with the measured value for at least the lipoprotein or lipoprotein subclass values identified as having an increased risk is drawn in red.

17. A method according to claim 16, further comprising drawing perimeter lines for the values not having increased risk associated therewith in black.

18. A method according to claim 15, wherein the plurality of selected lipoprotein subclass constituents include LDL particle concentration, LDL particle size, large HDL, and large VLDL.

19. A method according to claim 18, further comprising drawing a plurality of discrete boxes on the report one for enclosing each measured lipoprotein subclass value.

20. A method according to claim 19, wherein selected lipoprotein subclass constituent values on the report include a plurality of associated the risk-segment boxes in a respective risk analysis portion that are a plurality of horizontally spaced apart linearly aligned boxes that frame the numerical value or range of values associated with the risk defined fix each risk segment box in the respective risk analysis portion, wherein the perimeter line of the risk segment associated with the identified risk of the measured lipoprotein and/or lipoprotein subclass value box is a line having an increased line density and a contrasting color with respect to the boxes for the remainder of the risk segments in the respective risk analysis portions that are not associated with the identified risk of the measured lipoprotein subclass value.

21. A method according to claim 15, further comprising successively repeating the obtaining, analyzing, outputting, providing, and assigning steps for a plurality of different patient samples to thereby successively generate customized NMR-based lipoprotein risk assessments.

22. A method according to claim 15, wherein the measured lipoprotein values include the levels of the major lipoprotein constituents of total cholesterol, LDL cholesterol, HDL cholesterol, and triglycerides, as well as the measured lipoprotein subclass values of the size and/or concentration of LDL particles, the level of large HDL cholesterol, and the level of large VLDL.

23. A method according to claim 15, further comprising electronically transmitting the report to the clinician over a computer network.

* * * * *

UNITED STATES PATENT AND TRADEMARK OFFICE
CERTIFICATE OF CORRECTION

PATENT NO. : 6,653,140 B2
DATED : November 25, 2003
INVENTOR(S) : Otvos

It is certified that error appears in the above-identified patent and that said Letters Patent is hereby corrected as shown below:

Column 14,
Line 16, should read -- associated with the measured values; --
Line 53, should read -- analysis portions, --
Line 54, should read -- the box so that --

Column 15,
Line 34, should read -- LDL particles, the level of large HDL cholesterol, and the --

Column 16,
Line 56, should read -- a plurality of associated boxes in a respective --
Line 59, should read -- value or range of values associated with the risk defined for --

Signed and Sealed this

Twenty-fifth Day of May, 2004

JON W. DUDAS
*Acting Director of the United States Patent and Trademark Office*